(12) United States Patent
Alt

(10) Patent No.: US 6,478,815 B1
(45) Date of Patent: Nov. 12, 2002

(54) VASCULAR AND ENDOLUMINAL STENTS

(75) Inventor: Eckhard Alt, Ottobrunn (DE)

(73) Assignee: Inflow Dynamics Inc., Alexandria, VA (US)

( * ) Notice: Subject to any disclaimer, the term of this patent is extended or adjusted under 35 U.S.C. 154(b) by 0 days.

(21) Appl. No.: 09/663,896

(22) Filed: Sep. 18, 2000

(51) Int. Cl.[7] ................................................ A61F 2/00
(52) U.S. Cl. ..................................................... 623/1.15
(58) Field of Search ............................... 623/1.11, 1.12, 623/1.13, 1.14, 1.15, 1.16, 1.17, 1.18, 1.19, 1.2, 1.21, 1.22, 1.26; 606/198, 194, 191; 264/81, 219, 213; 600/1–3

(56) References Cited

U.S. PATENT DOCUMENTS 5,913,896 A  *  6/1999  Boyle et al. ................... 623/1
6,251,135 B1  *  6/2001  Stinson et al. .............. 623/1.34
6,287,332 B1  *  9/2001  Bolz et al. .................. 623/1.15

* cited by examiner

Primary Examiner—Michael J. Milano
Assistant Examiner—Vy Q. Bui

(57) ABSTRACT

A stent is composed of a single homogeneous tubing of niobium with a trace of additional metal less than about 5%, preferably zirconium, for alloy formation and reinforcement. The stent surface is provided with at least a partial coating to inhibit closure of a central lumen at a site of stent implant in the body. The surface coating may be vapor deposited or plasma deposited and comprises iridium oxide, titanium nitrate, a blend of metals, or surface oxidation of the niobium. The stent may have a rough surface characteristic.

21 Claims, 1 Drawing Sheet

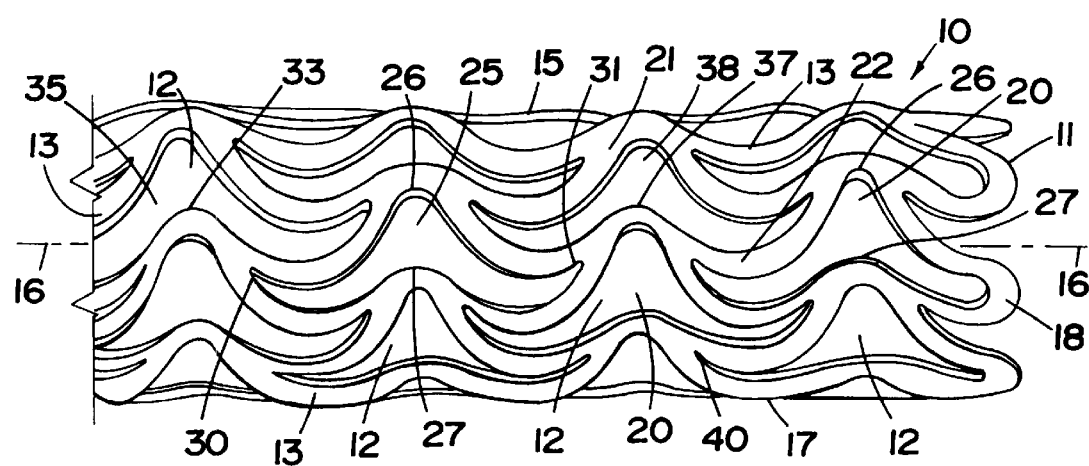

VASCULAR AND ENDOLUMINAL STENTS

CROSS-REFERENCE TO RELATED APPLICATIONS

This application is related to co-pending patent application Ser. No. 09/634,667, filed Aug. 8, 2000 ("the '667 application"), of the same inventor and assignee.

BACKGROUND OF THE INVENTION

The present invention relates generally to stents which are implantable or deployable in a vessel or duct within the body of a patient to maintain the lumen of the duct or vessel open, and more particularly to improvements in stent structures.

When inserted and deployed in a vessel, duct or tract of the body, for example a coronary artery after dilatation of the artery by balloon angioplasty, a stent acts as a prosthesis to maintain the vessel, duct or tract (generally referred to as a vessel for convenience herein) open. The stent has the form of an open-ended tubular element with openings through its sidewall to enable its expansion from a first outside diameter which is sufficiently small to allow the stent to traverse the vessel to reach a site where it is to be deployed, to a second outside diameter sufficiently large to engage the inner lining of the vessel for retention at the site.

An occluded coronary artery, for example, is typically attributable to a buildup of fatty deposits or plaque on the inner lining of the vessel. A balloon angioplasty procedure is the treatment of choice to compress the deposits against the inner lining of the vessel to open the lumen. Alternatively, removal of plaque may be achieved by laser angioplasty, or by rotationally cutting the material into finely divided particles which are dispersed in the blood stream. For a large segment of patients undergoing the procedure, traditional angioplasty has resulted in new blockage of the treated vessel only a relatively short time thereafter, attributable to trauma to the blood vessel wall from the original procedure. The mechanism responsible for this restenosis or re-occlusion of the vessel lumen is intimal hyperplasia, a rapid proliferation of smooth muscle cells in the affected region of the wall.

To maintain the vessel open, it has become customary to install a stent at the trauma site at the time of or shortly after the angioplasty procedure is performed. The stent is deployed by radial expansion under outwardly directed radial pressure exerted, for example, by active inflation of a balloon of a balloon catheter on which the stent is mounted. In some instances, passive spring characteristics of a preformed elastic (i.e., self-opening) stent serves the purpose. The stent is thus expanded to engage the inner lining or inwardly facing surface of the vessel wall with sufficient resilience to allow some contraction but also with sufficient stiffness to largely resist the natural recoil of the vessel wall.

The presence of the stent in the vessel, however, tends to promote thrombus formation as blood flows through the vessel, which results in an acute blockage. The thrombosis and clotting may be reduced or even eliminated by appropriate surface characteristics of the stent, sufficient to achieve this purpose. At the outward facing surface of the stent in contact or engagement with the inner lining of the vessel, tissue irritation can exacerbate restenosis attributable to hyperplasia.

Another factor affecting the choice of the stent and the stent material is allergic reaction to common stent materials suffered by a statistically significant percentage of the patient population subjected to stenting. These materials include chrome, nickel, and medical grade 316L stainless steel, which contains about 16% nickel. For such patients, the allergic reaction may be sufficient that stent implant is contraindicated. Wholly biodegradable stents of possibly sufficient radial strength are currently undergoing tests and may prove suitable in such cases.

Another consideration in material selection is the need for the implanting physician to be able to visualize the position of the stent during implantation to the desired target site in the body, and for purposes of examination from time to time thereafter at the implant site, typically by X-ray fluoroscopy. The wall of the stent must be sufficiently thick, depending on the stent material, not only to withstand the vessel wall recoil that invariably follows deployment at the target site, but to allow the stent to be seen on the fluoroscope. Various materials, such as 316L stainless steel, possess suitable mechanical strength. Typical stent wall or wire thicknesses have ranged from 70 to 200 microns (or micrometers, $\mu$m). A 70 to 80 $\mu$m thick 316L steel stent offers sufficient strength to resist recoil so as to maintain a lumen diameter close to the diameter achieved at full deployment by balloon inflation. This relatively thin and tiny metal structure creates little shadow on a fluoroscopic picture, however, since the X-ray absorption of the metal is low. Increasing the wall thickness of the stent to enhance its radiopacity and recoil resistance makes the stent less flexible, however, which adversely affects its maneuverability through narrow vessels and the amount of balloon pressurization necessary to enlarge the stent diameter sufficiently during deployment, with concomitant increased risk of balloon rupture.

It follows that a suitable stent for successful interventional placement should possess features of relatively non-allergenic reaction, good radiopacity, freedom from distortion on magnetic resonance imaging (MRI), flexibility with suitable elasticity to be plastically deformable, resistance to vessel recoil, sufficient thinness to minimize obstruction to flow of blood (or other fluid or material in vessels other than the cardiovascular system), and biocompatibility to avoid of vessel re-occlusion. Selection of the material of which the stent is composed, as well as design of the stent, plays an important role in influencing these features.

Aside from vascular usage, other ducts or tracts of the human body in which a stent might be installed to maintain an open lumen include the tracheo-bronchial system, the biliary hepatic system, the esophageal bowel system, and the urinary tract. Many of the same requirements are found in these other endoluminal usages of stents.

Despite improvements in the design and construction of coronary stents, restenosis remains a problem. A major contributing factor remains the inability of the body to incorporate the implanted foreign material quickly. Basic research with cell cultures and animal experiments have demonstrated that the degree of endothelialization of the foreign body determines the amount of the restenosis. Although it has been an assumption among industry practitioners and researchers that a highly polished and smooth surface is beneficial to prevent stent thrombosis and to facilitate endothelialization, experiments indicate this may not be entirely true.

A significant reason for the lack of a high clinical success rate with electropolished stents is the fact that the smooth muscle cells which seek to envelop a foreign body, such as a stent strut into the vessel wall, require a higher degree of proliferation to cover the foreign body. The continuing flow of blood with a high pressure and high shearing stress prevents the migration of smooth muscle cells, which proliferate from the media and adventitial cells of a stented vessel such as a coronary artery. It has been shown that a slightly rough surface considerably facilitates the coverage by smooth muscle cells, leading to a functional endothelial layer even after 10 to 14 days after stent implantation. A single layer of endothelial cells has been found to seal the neointima and thereby prevent the stimulus which facilitates and enhances the proliferation of cells beyond mere coverage of the foreign body.

The thinner the stent strut, the less the lumen of the stented vessel is obstructed. Moreover, a thin stent is more easily covered by a neoendothelial build-up. Accordingly, it is desirable to make the stent wall as thin as can be practically achieved. But the fluoroscopic visibility of stainless steel, for example, in a thickness below 60 $\mu$m is very poor because of the limited extinction of x-rays by such a thin metal tube.

Some improvement has been achieved by applying a suitable adherent material layer to stent core material of medical grade implantable 316L stainless steel. Layer materials have included gold and certain other noble metals, such as platinum. Such materials typically exhibit much greater radiopacity than stainless steel, that renders the stent highly visible under fluoroscopy as it is being advanced through the vessel lumen to the desired site of deployment, as well as after deployment. They are also substantially non-allergenic and non-thrombogenic. Such coating may be provided in a very thin layer, to enable the stent wall thickness to be determined almost solely by considerations of mechanical strength. Coatings, however, present a need for absolute adherence to the underlying metal of the stent to avoid cracking or defects in the homogeneous overlying layer, and sufficient resistance to peeling or flaking of the layer during insertion, and especially during expansion of the diameter of the stent as it is being deployed in final position in the artery at the target site, objectives which are not easily achievable.

The disadvantage of reduced mechanical strength of noble metals such as gold or platinum—which makes them unsuitable if sought to be used alone for application in the human vascular system—is overcome by the use of a core composed of a material such as stainless steel, having considerably better mechanical properties than the noble metal. But the presence of cracks or related defects in the surface coating can produce a galvanic potential which could ultimately lead to corrosion of the underlying steel or lesser metal, an unacceptable situation for a device intended to be permanently implanted in the body. Therefore, manufacturing requires a high degree of quality control and concomitant high cost.

Alternative or additional layers have also been used in stents. Applicant's U.S. Pat. No. (USPN) 6,099,561 discloses a stent structure having three fundamental layers, a first underlying layer of a base metal that functions to provide high mechanical strength, a second intermediate layer that functions to provide high fluoroscopic visibility—preferably a noble metal layer or alloy thereof—, and a top layer of a particularly beneficial biocompatible material—preferably a ceramic-like material such as iridium oxide or titanium nitrate. The intermediate layer of elemental or alloy of a noble metal is uninterrupted, highly adherent for tight coverage and substantially uniform thickness. Such an intermediate layer tends to assure avoidance of a galvanic potential that would lead to corrosion of the lesser, base metal, including such a condition that may obtain with a layer of ceramic-like metal overlying the base metal at points where fissures might exist were it not for the uninterrupted presence of the intermediate noble metal layer. The three layer stent of the '561 patent exhibits mechanical strength, small physical dimensions, increased visibility, long-term stability, and a highly biocompatible surface that enables rapid endothelialization with low occurrence of restenosis.

SUMMARY OF THE INVENTION

The present invention provides a stent adapted to be expanded from a first vessel-navigable diameter to a larger second vessel-deployed diameter, which is composed of material that possesses all of the desirable attributes mentioned above and yet can be fabricated in a single homogeneous structure without need for additional layers. In the preferred embodiment the stent material is niobium with a sufficient amount of zirconium added, typically less than 5% by weight, for hardness of the combination. The stent may thus be fabricated from a single piece of tubing at relatively low cost and yet with all of the desirable features of non-allergenic reaction, excellent and adequate radiopacity (density twice that of stainless steel), distortionless for MRI, highly flexible, sufficiently elastic to be plastically deformable, non-brittle, sufficient strength to resist vessel recoil, and sufficient thinness to minimize obstruction to blood flow, and highly biocompatible. The niobium/zirconium material is also oxidizable to provide surface passivation. This material is readily treatable by post-processing such as annealing, electropolishing for rounded edges, and so forth.

Additional surface modification or other substances or agents may be applied to the stent surface, such as vapor deposition of even more highly biocompatible layers, to preclude occlusion from restenosis or thrombosis during the acute stage following deployment of the stent. For example, iridium and iridium oxide, titanium nitrate, or compositions such as described in U.S. Pat. No. 5,679,815, might be applied.

The stent might also be formed from a sintering process with small microspheres by heat and pressure (e.g., such as disclosed in U.S. Pat. No. 5,198,187), thereby avoiding costly production and control steps.

BRIEF DESCRIPTION OF THE DRAWING

The above and still further aims, objectives, features, aspects and attendant advantages of the present invention will become apparent to those skilled in the art from the following detailed description of a best mode presently contemplated of practicing the invention by reference to certain preferred embodiments and methods of manufacture thereof, taken in conjunction with the sole FIGURE of drawing which shows a side view of a preferred stent structure for the invention (in which the far side is not shown for the sake of simplicity).

DETAILED DESCRIPTION OF THE BEST MODE OF PRACTICING THE INVENTION

The sole FIGURE is a perspective view (not to scale) of a stent 10 in the form of a hollow tubular self-supporting structure composed of niobium and zirconium, preferably less than 5% zirconium and more preferably approximately 2% zirconium, with the remainder niobium. The added zirconium provides desirable physical characteristics to the stent.

The tubular stent member is provided with a multiplicity of through-holes or openings 12 through sidewall 15, defined and bounded by a plurality of struts or links 13, which enables expansion of the stent diameter when the device is to be deployed at a target site in a vessel, duct or tract of the human body. The openings 12 may be precisely cut out to form a latticework sidewall using a narrow laser beam of a conventional laser following a programmable pattern. The removed material that formerly occupied openings 12 is discarded following the cutting.

By way of example and not of limitation, the resulting pattern in the latticework sidewall 15 is a network of interconnected struts 13 which are optimized for orientation predominantly parallel to the longitudinal axis 16 of the tube 11, with none of the struts oriented perpendicular (i.e., transverse) to the axis 16, so that no strut interconnecting any other struts in the latticework is oriented to lie completely in a plane transverse to the longitudinal axis, without running from one end of the stent to the opposite end. This type of structure, which is described in detail in applicant's co-pending application Ser. No. 08/933,627, provides a relatively very low friction characteristic (or coefficient of friction) of the outer surface 17 of the stent, to ease advancement of stent 10 in a vessel, duct or tract to a site for deployment. The network or latticework of struts 13 may define a series of longitudinally repeating circumferential rows 20 of openings 12, in which each opening has a shape which resembles the outline of a handlebar moustache, or of a Dutch winged cap, with each opening bounded by alternating links in wavelets of higher and lower crests in successive rows of each circumferential column displaced along the length of the cylindrical element. If viewed upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element.

Each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions will then fit into each other, as the pattern formed by the latticework of struts allows substantial nesting together of the crests and bows, which assures a relatively small circumference of the stent in the crimped condition. Such a stent is highly flexible, and is capable of undergoing bending to a small radius corresponding to radii of particularly tortuous coronary arteries encountered in some individuals, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. The particular configuration of the stent structure, while highly desirable, is illustrative only and not essential to the principles of the present invention.

The stent may be pre-opened after fabrication to relieve stresses. Pre-opening produces a stent inner diameter that allows the stent to slide comfortably over the uninflated mounting balloon, for ease of crimping the stent onto the balloon. Annealing may be performed after preopening by heating the stent structure to an appropriate temperature for a predetermined interval of time.

The niobium/zirconium material of which the stent is composed is fabricated in any conventional manner for producing alloys, with the zirconium amounting from 1% to 5% by weight, preferably about 2%, and the remainder niobium. For example, the manufacturing process may be performed by sintering particles or microspheres of the constituent metals under heat and pressure. Rather than using zirconium as the trace metal, a trace amount (e.g., one to three percent) of titanium or tantalum may be alloyed with the niobium for added strength and other desirable physical characteristics. Other suitable alternative additive materials include those described in U.S. Pat. Nos. 5,472,794 and 5,679,815, for example. The alloy is then formed into tubing and the through holes are provided in its side wall as by laser cutting.

The stent structure can be produced with a wall thickness of about 85 $\mu$m, which offers sufficient mechanical strength to resist the natural recoil of the blood vessel wall following deployment of the stent, as well as excellent visibility under fluoroscopy, but which does not obstruct the vessel lumen to any significant extent. Since it has none of the distortion encountered with metallic 316L stents to MRI, use of the niobium-based stent in noninvasive monitoring also of cerebral and peripheral vessels is highly beneficial.

Surface modification of the stent to apply a desired coating such as iridium oxide or titanium nitrate may be achieved by vapor deposition or plasma deposition, or other conventional method. Such modification may be used to give the stent a rough surface. Alternatively, the surface may be passivated only, by oxidation of the niobium for reduced immunoresponse and less thrombogenicity.

Although a best mode of practicing the invention has been disclosed by reference to certain preferred embodiments and methods, it will be apparent to those skilled in the art from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A stent composed of a single homogeneous, substantially non-decomposing tubing consisting solely of niobium except for a trace in a range from about 1% to about 5% by weight of at least one additional metal selected from the group consisting of zirconium, titanium and tantalum for alloy formation and reinforcement.

2. The stent of claim 1, wherein said trace metal is zirconium.

3. The stent of claim 1, wherein the amount of trace metal in the stent composition is less than 5% about 2%.

4. The stent of claim 3, wherein said trace metal is zirconium.

5. The stent of claim 1, wherein the stent has at least a partial surface coating to inhibit closure of a central lumen at a site of stent implant in the body.

6. The stent of claim 5, wherein said surface coating is iridium oxide.

7. The stent of claim 5, wherein said surface coating is titanium nitrate.

8. The stent of claim 5, wherein said surface coating is a blend of metals.

9. The stent of claim 5, wherein said surface coating is oxidation of the niobium.

10. The stent of claim 1, wherein the stent has a rough surface characteristic.

11. A method of fabricating a stent which comprises forming a single homogeneous, substantially non-decomposing tubing consisting solely of niobium alloyed with only a trace in a range from about 1% to about 5% by weight of at least one additional metal selected from the group consisting of zirconium, titanium and tantalum for reinforcement.

12. The method of claim 11, wherein said trace metal is zirconium.

13. The method of claim 11, wherein the amount of trace metal in the alloy composition is 5% about 2% by weight.

14. The method of claim 11, including at least partially coating the stent surface to inhibit closure of a central lumen at a site of stent implant in the body.

15. The method of claim 14, including performing said surface coating by vapor or plasma deposition.

16. The method of claim 14, including applying iridium oxide as said surface coating.

17. The method of claim 14, including applying titanium nitrate as said surface coating.

18. The method of claim 14, including applying a blend of metals as said surface coating.

19. The method of claim 14, including passivating the surface by oxidation of the niobium as said surface coating.

20. The method of claim 11, including forming a rough surface on said stent.

21. The method of claim 11, including fabricating the stent by sintering particles of the alloy materials under heat and pressure.

* * * * *